United States Patent [19]

Gaskill, III

[11] Patent Number: 4,911,717
[45] Date of Patent: Mar. 27, 1990

[54] INTRAVASULAR ARTIFICIAL ORGAN

[76] Inventor: Harold V. Gaskill, III, 6118 Saddlebow, San Antonio, Tex. 78240

[21] Appl. No.: 63,313

[22] Filed: Jun. 18, 1987

[51] Int. Cl.$^4$ .......................... A61F 2/04; A61M 5/00
[52] U.S. Cl. .................... 623/11; 604/891.1; 623/66
[58] Field of Search ...................... 604/53, 175, 891.1; 623/10, 11, 12, 1, 66; 128/1 R

[56] References Cited

U.S. PATENT DOCUMENTS

| | | | |
|---|---|---|---|
| 3,093,831 | 6/1963 | Jordan | 623/12 |
| 3,734,851 | 5/1973 | Matsumura | 210/22 |
| 4,286,584 | 9/1981 | Sampson et al. | 623/66 |
| 4,309,776 | 1/1982 | Berguer | 128/1 R |
| 4,402,694 | 9/1983 | Ash et al. | 623/12 |
| 4,409,331 | 10/1983 | Lim | 623/11 |
| 4,432,752 | 2/1984 | Marlon | 604/53 |
| 4,588,407 | 5/1986 | Isono | 623/11 |
| 4,673,394 | 6/1987 | Fenton, Jr. et al. | 604/175 |

OTHER PUBLICATIONS

Altman et al., Diabetes, 35: 625 (Jun. 1986).
Tze et al., Diabetologia, 19:541 (1980).

Primary Examiner—Richard J. Apley
Assistant Examiner—David J. Isabella
Attorney, Agent, or Firm—Iver P. Cooper

[57] ABSTRACT

The intravascular artificial organ is comprised of a flexible, hollow, semipermeable catheter containing living cells or tissue. The catheter is constructed of material with a pore size resulting in a molecular weight cutoff of approximately 50,000 Daltons. This pore size permits oxygen, glucose, and hormones to diffuse freely into and out of the organ. By contrast, cells of the host immune system cannot gain access to the cells or tissues within the organ and destroy them. Thus, it is possible to load the intravascular artificial organ with cells and tissues of immunologically foreign individuals, animals, bacteria or plants. The preferred embodiment consists of a double lumen catheter connected to two percutaneous access ports permitting flushing and reloading of the organ without removing it from the body.

19 Claims, 3 Drawing Sheets

INTRAVASULAR ARTIFICIAL ORGAN

BACKGROUND OF THE INVENTION

1. Field of the Invention

This invention relates to the use of an intravascular artificial organ to deliver hormones and other biologically producible substances to the human body for the treatment of endocrine (secretory) organ failure and other conditions.

2. Information Disclosure Statement

One example of endocrine organ failure which this device can treat is diabetes.

Diabetes results when the pancreas is not able to secrete enough of the hormone insulin. Insulin regulates the metabolism of glucose in the body. Failure of the pancreas to produce insulin in sufficient quantities results in the accumulation of high levels of glucose in the blood after oral intake of foods containing glucose. For reasons which are not yet understood, this causes injury to the blood vessels of the eye, kidneys, and other tissues of the body. Blindness, kidney failure, and amputation are among the sequelae of diabetes.

Once it was recognised that diabetes was caused by insufficient insulin levels, it became possible to treat diabetes by giving insulin injections. It was learned that the insulin molecule produced by both pigs and cows was effective in humans. Insulin extracted from the pancreatic issue of these animals was injected into the bodies of diabetics several times each day. This method of treatment prevented the death of thousands of people with diabetes. It was soon recognised that frequent injections of insulin were difficult to maintain for a lifetime. The insulin molecule was therefore combined with other elements such as zinc to prolong its action. This enabled treatment by injections once or twice daily in many patients. A number of problems remained. First, it was only possible to estimate the average insulin requirement. Increased dietary intake resulted in abnormally high blood glucose levels. Alternatively, blood glucose would be abnormally low if meals were skipped. Some patients were unable to manage their strict dietary requirements and insulin injection schedules. Many of these patients succumbed to their disease. Others suffered the complications of diabetes mentioned above.

It has long been recognized that restoring normal pancreatic endocrine function to diabetics would be a dramatic breakthrough in the treatment of this disease. There have been several approaches to this end.

First, transplantation of human or animal pancreatic tissue or islet cells into diabetics has been attempted by many groups. (See Sutherland, et al., Transplantation Proceedings, 19:291–297(181); Sutherland, Diabetologia, 20:161–185(1981); Naji, Surgery, 86:218–224(1979)). There are several problems with this approach. The most significant of these problems is that the transplanted tissue is recognized as foreign by the immune system of the recipient. This foreign tissue is then destroyed by the recipient's body. Attempts to suppress the immune system of the recipient are complicated by increased susceptibility to infection and cancer. A second problem is caused by other materials secreted by pancreatic tissue. In addition to insulin, the pancreas produces enzyme which aid in the digestion of meat. Transplanted pancreatic tissue secretes these enzymes, which then interfere with healing after the transplant operation.

Second, mechanical pumping devices of various design have been used to deliver insulin to diabetics on a continuous basis. One of the major problems with this approach is that the pump must deliver insulin at a rate proportional to the glucose in the blood. Continuous measurement of blood glucose and feedback to the pumping device have proven to be a major stumbling block. In addition, mechanical devices require an energy supply and are prone to failure. A practical mechanical pancreas substitute does not exist at this time.

The third approach has been to enclose pancreatic tissue from other people or animals in a semipermeable enclosure. By selecting a material with a pore size of approximately 50,000 Daltons, it is possible for oxygen and glucose to diffuse into the foreign tissue. The tissue produces insulin in quantities proportional to the concentration of glucose present. This insulin then diffuses out of the enclosure and throughout the rest of the body. Although oxygen, glucose, and insulin can flow through the pores, cells and immunoglobulins of the recipient immune system cannot. Thus, the pancreatic tissue is protected from the host's immune system.

This system has bee used to restore normal glucose metabolism to diabetic rats. Pancreatic tissue was enzymatically digested, and the insulin-secreting units called islets extracted and concentrated. The islets were then loaded into capillary tubes made of a suitable semipermeable polymer, and these capillaries were implanted in the peritoneal cavity of rats previously made diabetic by treatment with streptozocin (a pancreatic poison). Approximately half of the animals so treated demonstrated normal glucose metabolism one year later. (Altman, et al., Diabetes, 35:625(June 1986)).

Attempts to adapt this technique to larger animals have been based on construction of an implantable chamber containing pancreatic islets in a suitable growth medium. This chamber contains a conduit constructed of suitable semipermeable membrane. The resulting device is then connected between an artery and a vein, resulting in blood flow through the device. (Tze, et al., Diabetologia, 19:541(1980); Sun, et al., in BIOCOMPATIBLE POLYMERS SCIENCE AND TECHNOLOGY, Chap. 40, p 929 Szycher, ed.;1983)). These devices have been proven impractical because blood flowing through the devices tends to clot, thus rendering them useless.

Jordan, U.S. Pat. No. 3,093,831 describes a primitive artificial gland comprising a semipermeable bag holding glandular tissue. The bag is tied closed, and its pores have a molecular weight cutoff of no more than 10,000–15,000 Daltons. As noted by Jordan, this permits free passage of steroid hormones and many nutrients, but not of the immunoglobulins. The bag was preferably tubular in form with a diameter of 4 mm or less, so as to assure easy diffusion of nutrients.

Jordan taught that this artificial gland could be implanted into the body in a manner so as to be in contact with the bloodstream, the artificial gland taking over the function of the natural gland, and the body regulating its activity and supplying it with nutrients.

Like Jordan's artificial gland, my intravascular artificial gland allows hormones to be supplied to the body under metabolic control and without continual injections to maintain the hormone supply. However, my gland is more suitable for prolonged use. If cells in Jordan's artificial gland die, or lose their secretory function, there is no ready means of replacing them. Nor is there any convenient method for eradicating an infectious agent which lodges itself in the gland, other than systemic treatment. Additionally, the cord with which Jordan fastens his bag may loosen in the harsh chemical environment of the bloodstream, thereby exposing the tissue to immunological attack.

Jordan's artificial gland is also vulnerable to mechanical strains which would damage the gland cells or rupture the container. While it may be implaced in the bone marrow as a protective measure, this might occasion some discomfort for the patient and might interfere with bone growth. The protective shield suggested by Jordan as an alternative might be dislodged by heavy physical exertion.

Lim, U.S. Pat. No. 4,391,909 teaches encapsulating living tissue in semipermeable microcapsules without impairing viability and injecting these microcapsules into a patient. While the capsules may be engineered to have a predetermined life, it is not possible to decide, after injection, to cease production of the substance secreted by the encapsulated tissue based on observation of the patient's clinical signs. (See also Seften, U.S. Pat. No. 4,353,888).

Matsumura, U.S. Pat. No. 3,734,851 descries a dialysis device in which liver cells are held within semipermeable membranes. Blood is extracted from the body and passed over the membranes. Metabolites pass from the liver cells to the blood, and enter the body when the blood is returned to the patient. While the cells are readily accessible, the need for extracorporeal processing tends to limit use of the device.

Berguer, U.S. Pat. No. 4,309,776 describes an islet cell culture device designed for implantation either as a "button" in the wall of a blood vessel or as a "sieve" in an arteriovenous fistula. The device has a chamber 12 and a tube 14 whereby cells may be injected into the chamber. The chamber has a semipermeable wall 18. The chamber, once implanted, cannot be readily repositioned, and there is no means for withdrawing dead cells.

Isono, U.S. Pat. No. 4,588,407 describes an extracorporeal artificial organ, with a preferred coating on the parts in contact with body fluid.

Indwelling catheters have frequently been used to deliver drugs to patients over prolonged periods. (See Marlon, U.S. Pat. No. 4,432,752; Pevsner, U.S. Pat. No. 4,509,523; Gordon, U.S. Pat. No. 4,531,936; Yates, U.S. Pat. No. 4,531,937). However, the adaptation of a catheter for intravascular organ, tissue or cell culture is novel.

SUMMARY OF THE INVENTION

One component of my artificial organ is a flexible, hollow, at least partially semipermeable catheter having a cell culture chamber adapted to receive living cells or tissue, the catheter being designed for intravascular emplacement. The pore size of the chamber wall is selected to permit free diffusion of the secretory products, and of nutrients, but to block the entry of immunoglobulins or immunocytes. The artificial organ may thus be loaded with immunologically foreign cells or tissues.

While, in a preferred embodiment, the cell culture chamber holds pancreatic tissue, this invention is not so limited. Any kind of living cells or tissues, including animal, plant and bacterial cells, may be placed in the chamber. The substance which they produce may be one endogenous to the cells, or it may be one which they express only as a result of genetic manipulation. The substance need not itself be naturally occurring, provided that it can be produced by an appropriately manipulated cell given a proper substrate or nutrient. Thus, while in a preferred embodiment the device is used to treat diabetes, it may also be used for other purposes.

By placing the semipermeable portion within the lumen of a large blood vessel, it is constantly bathed by flowing blood. This ensures that the tissue contained is supplied with oxygen, glucose, and electrolytes. In addition, secretory or excretory products of the contained tissue diffuse into the host circulation rapidly. Because the blood is flowing through a native vessel, it is less likely to form clots which would interfere with the function of the organ.

The second component is a tethering conduit connected to the catheter. This conduit anchors the catheter in place, and provides a means for withdrawing it from the body. The tethering conduit also features an entry portal by which cells and tissues may be introduced into the catheter through said conduit.

DETAILED DESCRIPTION OF THE INVENTION

Figure 1:
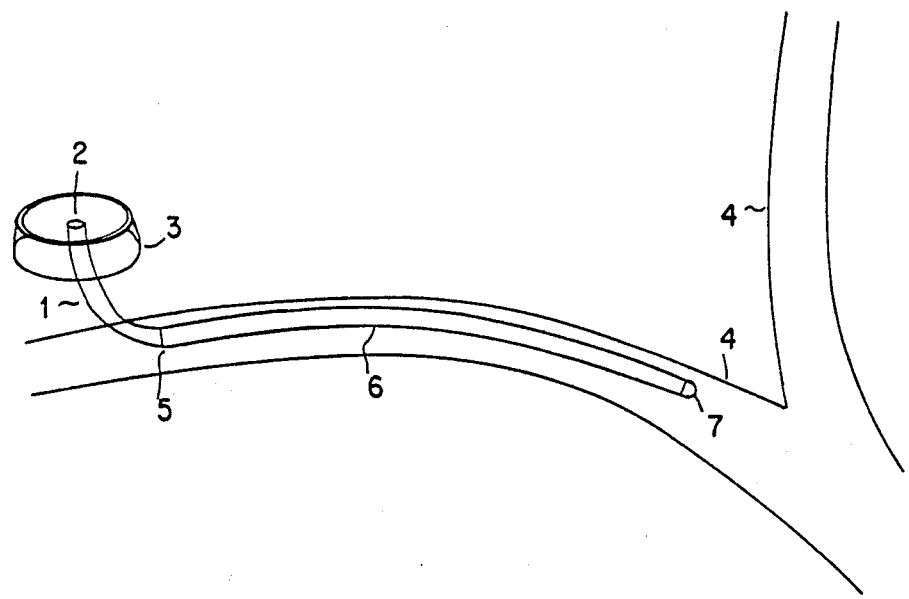
FIG. 1 shows a simple embodiment of the device with a single port located just below the skin leading to the semipermeable catheter, the latter resting wholly within a large vein.

The simplest embodiment of the device is seen in FIG. 1. The proximal end of the device consists of an access port consisting of a body 3 with an injection port 2 constructed of a soft polymer plug such as compressed silicone rubber. This polymer plug seals conduit 5 leading to the semipermeable portion of the device 6. The proximal portion of this conduit is constructed of a biologically inert material which will resist penetration by a hypodermic needle. Suitable materials would include stainless steel, titanium, vanadium, polycarbonate, polytetrafluoroethylene, or carbon. The distal portion of the tethering catheter is constructed of a semi-rigid biologically inert material such as silicone, polyvinyl, polyethylene, polypropylene, or polyurethane. This material should have enough rigidity to hold the semipermeable portion in position within the blood-vessel. The tethering conduit is connected to the semipermeable portion of the device 6. This portion is constructed of a biologically inert polymer manufactured in a manner which makes the material semipermeable with a molecular weight cut-off of approximately 50,000 Daltons. One such polymer is XM-50 vinyl-copolymer manufactured by Romicon, Inc., 100 Cummings Park, Woburn, Mass. 01801, and discussed in Breslow, et al., "Advances in Hollow Fiber Ultrafiltration Technology" in POLYMER SCIENCE AND TECHNOLOGY, Vol. 13, pp 109–127 (Cooper, ed.:1980). An alternative polymer is Biomer segmented polyurethane manufactured by Ethicon, Inc., Highway 22, Somerville, New Jersey, 08876. Many other polymers in this family may be suitable. Their general properties are discussed in "Biomedical Polyurethanes," in POLYURETHANES AND MEDICINE, Chapter 5, pp 57–71 (Lelah and Cooper ed:1986)

The distal end of the semi-permeable catheter is sealed by a plug 7.

Practical application of the device for treatment of Type I diabetes or primary endocrine failure of the pancreas would be as follows: the device would be constructed and sterilized by standard techniques. Pancreatic tissue would then be harvested in sterile fashion from another human being or from an animal such as a pig or cow. The pancreatic tissue would be processed and the islets extracted by standard techniques.

Several methods for the extraction and purification of islets of Langerhans are described in Muller-Ruchholtz, et al., Transplantation Proceedings, 19:911–915 (February 1987); Alderson, et al., Id., 19:916–917; Rajotte, et al., Id., 19:918–922. However, this invention is in no way dependent on the use of any particular extraction or purification technique.

Depending on the efficiency of islet recovery, more than one donor pancreas may be required. Between one and two grams of pure, sterile islet tissue are likely to be necessary.

The sterile artificial intravascular organ is then loaded with islets. Under aseptic conditions, a small (27 gauge) hypodermic needle is pushed through the plug in the distal end of the semipermeable catheter taking care not to damage the catheter wall. This needle serves as a vent to allow the escape of air as the port is loaded. The sterile islet tissue is then loaded into the organ via the proximal port. This is accomplished by piercing the polymer septum on the port with a hypodermic needle and infusing the islets as the residual air in the port is vented through the needle in the distal end of the port. Once the organ is loaded with islets, it must be implanted in the patient immediately or provisions made to supply the living tissue within the catheter with oxygen and nutrients.

The procedure for implanting the organ in the recipient is relatively simple and can be performed under local anesthesia. The most suitable site for implant is below the collar-bone or clavicle. With the patient in the supine position, the neck, shoulder, and chest are prepared with a surgical scrub such as providone iodine or chlorhexidine gluconate. Sterile drapes are then placed with exposure of the clavicle an upper chest. The operating table is then tilted on an incline with the feet of the patient about thirty centimeters above the head. This increases the pressure in the veins in the upper part of the body, making them larger and more easily located. In addition, the increased pressure reduces the chance of air entering the vein during the operation.

A suitable location for the organ is the vein below the clavicle. This is the so-called subclavian vein, which drains the arm. Although other large veins would be satisfactory, the subclavian vein is close to the surface of the skin, which makes it more easily accessible. It has a relatively high flow rate, which makes clotting of the blood less likely. In addition, if clotting should occur, other veins in the area can usually provide adequate drainage of the arm, thus minimizing the risk to the patient. This vein is often used as a site for placement of indwelling medical appliances such as cardiac pacemakers and dialysis catheters. Another suitable location is the subclavian artery. Placing the catheter in an artery has the advantage that arterial blood carries twice as much oxygen. However, because of the higher pressure, bleeding is more likely to adversely affect the patient's health. Whether an arterial or venous location is chosen, the vessel preferably has a diameter of at least 5 mm, to avoid clotting.

The procedure for placing tubular devices in blood vessels is well-known to surgeons. Although there are many variations in the technique, the following approach is typical. First, the area under the clavicle is infiltrated with local anesthetic such as xylocaine. An incision approximately 5 centimeters in length is then created below and parallel o the clavicle. Next, a subcutaneous pocket large enough to hold the artificial organ is created. A hollow hypodermic needle is placed through the incision and into the lumen of the vessel. A flexible coiled steel guide-wire approximately 50 centimeters in length is then passed through the needle and into the vein for a distance of twenty centimeters. The needle is then removed as the guide-wire remains in the vessel. A rigid, tubular dilator with a tapered front-end, a diameter equal to the device to be implanted, and a surrounding hollow sheath, is then slid over the guide-wire and pushed into the vessel, thus creating a passage of suitable dimension from the skin to the vessel. The intravascular organ, loaded with living islets, is then placed in the pocket just below the skin. The dilator and guide-wire are now removed from the sheath surrounding them. The catheter section of the artificial organ is pushed through the sheath until it resides in the vessel as depicted in FIG. 1. The sheath is then peeled away. The skin is then closed with surgical suture. A radiograph of the chest is then obtained to confirm that the catheter is in the proper position.

Figure 2:
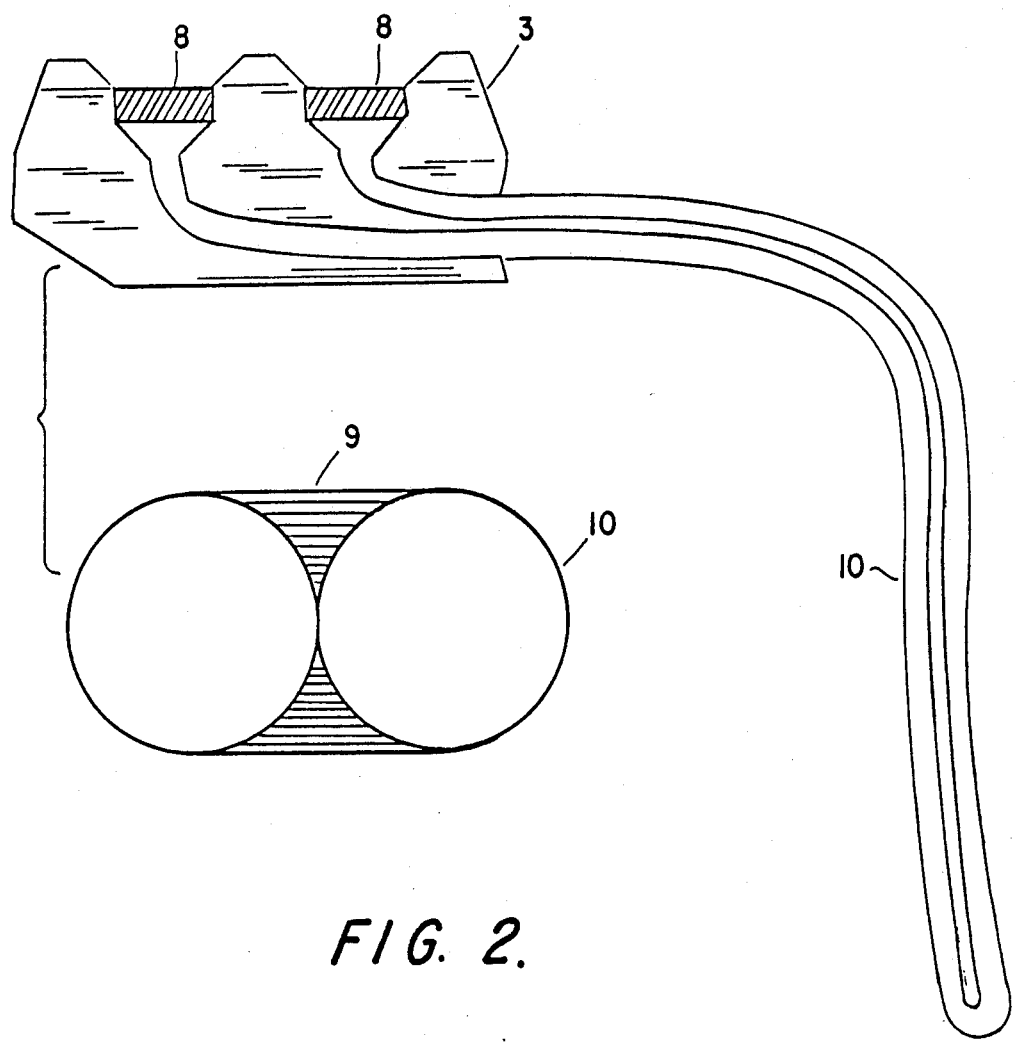
FIG. 2 shows the preferred embodiment of the device, which offers a dual access port connected to a semipermeable double lumen catheter.

The preferred embodiment pictured in FIG. 2 is implanted similarly. The advantages of this embodiment are that the proximal and "distal" ends of the organ are now both located just below the skin. This has several advantages. First, the artificial organ may be implanted in an empty state and loaded with cells or tissue at a separate time. This is accomplished by preparing the skin in sterile fashion outlined above and passing two hypodermic needles through the skin, through the polymer septa, and into the port. One needle serves as an entry site while the second serves as a vent. Using this technique, the artificial organ can be implanted in the operating room and the patient allowed to recover. Days or weeks later, the patient can have the artificial organ loaded with cells or tissue as described above. A second advantage of the dual port system is that it is possible to access the artificial organ at a later time with a minimum of difficulty or risk to the patient. This would be useful in cases of possible bacterial infection of the artificial organ. Cultures could be obtained from the organ to confirm the presence of bacteria. Antibiotic solutions could also be added to treat the infection. If the cells or tissues in the artificial organ aged or their function deteriorated for any reason, they could easily be flushed and replaced. The function of the organ could be modified by altering the concentration of cells in the organ. Alternatively, mixtures of cells or tissues with different biologic properties could be combined in varying proportion with relative ease.

As with any foreign object implanted in the body, infection and malfunction are possible. One of the advantages of the present design is that it does not require a major procedure to be implanted. Nor does it alter the native anatomy of the host. Moreover, in the event of failure it may be removed easily and safely. This is accomplished by opening the incision under sterile conditions and withdrawing the port from the pocket and the artery or vein. The wound is then closed and a pressure dressing applied. In most cases, healing should follow without permanent dysfunction.

Several modifications are possible and may be necessary or desirable in the final design. First, it may be useful to connect the intravascular portion of the device to the subcutaneous ports by a longer double-lumen catheter which does not lie within the blood vessel. This would enable placement of the device in the lumen of large vessels deep within the body while still retaining access via the subcutaneous ports.

Another possible modification relates to the problem of blood clotting. Although this problem should be greatly reduced by placement within the blood vessel, additional measures may be needed to reduce the incidence still further. Among the possible techniques would be treatment of the exterior surface of the catheter with various materials which are biocompatible even after prolonged contact with blood. (See Kambic, et al., Chapter 8, pp. 179-198, BIOCOMPATIBLE POLYMERS SCIENCE AND TECHNOLOGY (Szycher, ed.:1983)).

Figure 3:
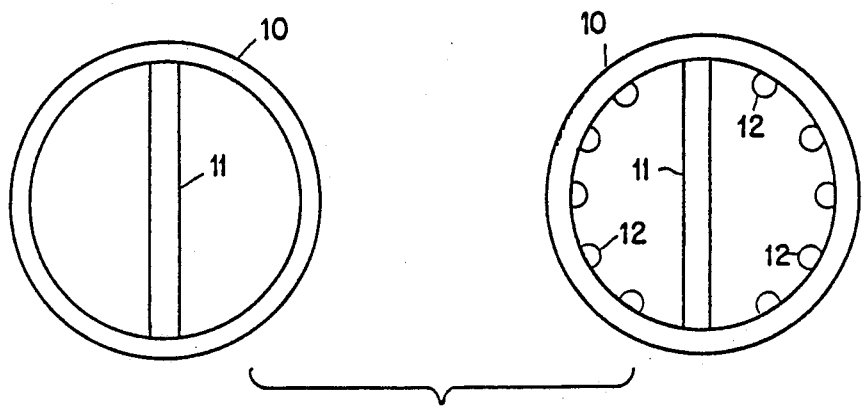
FIG. 3 shows a cross-section of a preferred embodiment of the catheter. The right panel shows a catheter with a longitudinal supporting element; the catheter on the left side lacks this feature.

It may also be advantageous to provide strengthening or supporting elements as shown in FIG. 3. These elements may be longitudinal, circular or helical in configuration, and may take the form of a grid or mesh.

I claim:

1. A method of delivering a biosynthetic substance to a patient comprising (a) inserting into a blood vessel of a patient a catheter closed at one end and having a cell culture chamber, said chamber being adapted to receive and maintain functional cells or tissues which produce a desired biosynthetic substance, said chamber having a wall, at least a portion of said wall being permeable to said substance and to nutrients provided by the blood which are necessary to maintain the cells or tissues in a functional state, said wall being impermeable to immunocytes and immunoglobulins; and (b) tethering said catheter in place in the blood vessel by tethering means, whereby the wall of the cell culture chamber is constantly bathed by blood flowing in said blood vessel, said tethering means further providing conduit means whereby cells or liquids may be introduced into or withdrawn from said chamber; said desired biosynthetic substance being produced by said cells and delivered through said wall directly into the bloodstream of the patient.

2. The method of claim 1 in which the cells are introduced into the chamber before the catheter is inserted into the blood vessel.

3. The method of claim 1 in which the cells are introduced into the chamber after the catheter is inserted into the blood vessel.

4. The method of claim 1 in which the blood vessel is a vein.

5. The method of claim 4 in which the vessel has a diameter of at least 5 mm.

6. The method of claim 4 in which the vein is the subclavian vein.

7. The method of claim 1 in which the substance is insulin.

8. The method of claim 7 in which the tissue is pancreatic islet tissue.

9. The method of claim 1 in which the chamber wall is formed of a semipermeable membrane having a molecular weight cut-off of about 50,000 Daltons whereby entry of immunoglobulins is prevented.

10. The method of claim 1 in which cells or tissue are no longer functional are removed from the culture chamber through said conduit means.

11. The method of claim 1 in which a therapeutic agent is introduced through said conduit into said chamber and thence into the bloodstream.

12. The method of claim 11 in which the agent is an antibiotic.

13. The method of claim 1 in which, after insertion, the composition of the cells within the chamber is modified without removing the catheter from the patient.

14. The method of claim 1 in which the conduit means is a double lumen conduit means, and cells or liquid are introduced through one lumen and withdrawn through the other lumen.

15. The method of claim 1, said conduit means comprising subcutaneous port means at the end distal to said cell culture chamber, and wherein said catheter is implanted so that said port means assumes a subcutaneous position.

16. The method of claim 15 wherein said port means comprises a septum pierceable by a hypodermic needle.

17. The method of claim 16 wherein cells or substances are introduced into or withdrawn from said culture chamber by piercing said septum with a hypodermic needle and getting cells or substances from or drawing them into said needle.

18. The method of claim 1 wherein the tethering means is sufficiently rigid to hold the chamber in position within a blood vessel.

19. The method of claim 1 wherein the portion of the exterior surface of the catheter which is intended to come into prolonged contact with blood is treated with an agent to reduce the incidence of blood clotting thereon.

* * * * *